United States Patent
Deng

(10) Patent No.: US 8,097,750 B2
(45) Date of Patent: Jan. 17, 2012

(54) CINCHONA ALKALOID-CATALYZED ASYMMETRIC MANNICH REACTIONS

(75) Inventor: Li Deng, Newton, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 11/954,853

(22) Filed: Dec. 12, 2007

(65) Prior Publication Data

US 2008/0228000 A1 Sep. 18, 2008

Related U.S. Application Data

(60) Provisional application No. 60/875,900, filed on Dec. 20, 2006.

(51) Int. Cl.
*C07C 229/00* (2006.01)
*C07D 453/04* (2006.01)
(52) U.S. Cl. ........................................ 560/155; 546/134
(58) Field of Classification Search ........................ None
See application file for complete search history.

(56) References Cited

U.S. PATENT DOCUMENTS 4,232,165 A * 11/1980 Hagen et al. ............... 548/327.1

FOREIGN PATENT DOCUMENTS

WO WO-2005/121137 A1 12/2005

OTHER PUBLICATIONS

Tillman et al. Chem Commun. 2006, 1191-1193.*
Palomo et al. J. Am. Chem. Soc., 2005, 127(50), 17622-17623.*
Shaus et al. J. Org. Chem., 2007, 72 (26), 9998-10008.*
Barnes, D.M. et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," J. Am. Chem. Soc., 124(44):13097-13105 (2002).
Berner, O.M. et al., "Asymmetric Michael Additions to Nitroalkenes," Eur. J. Org. Chem., 1877-1894 (2002).
France, S. et al., "Nucleophilic Chiral Amines as Catalysts in Asymmetric Synthesis," Chem. Rev., 103(8):2985-3012 (2003).
Li, H. et al., Enantioselective Nitroaldol Reaction of α-Ketoesters Catalyzed by Cinchona Alkaloids, J. Am. Chem. Soc., 128(3):732-733 (2006).
Li, B-J et al., "Asymmetric Michael Addition of Arylthiols to α,β-Unsaturated Carbonyl Compounds Catalyzed by Bifunctional Organocatalysts," Letter, 4:603-606 (2005).
Liu, T-Y et al., "Enantioselective Construction of Quaternary Carbon Centre Catalysed by Bifunctional Organocatalyst," Org. Biomol. Chem., 4:2097-2099 (2006).
Ma, D. et al., "Diastereoselective Henry Reactions of N,N-dibenzyl α-amino aldehydes with Nitromethane Catalyzed by Enantiopure Quanidines," Tetrahedron Letter, 43:9401-9403 (2002).
Marcelli, T. et al., "Cinchona Derivatives as Bifunctional Organocatalysts for the Direct Asymmetric Nitroaldol (Henry) Reaction," Letter, 18:2817-2819 (2005).
McCooey, S.H. et al., "Urea- and Thiourea-Substituted Cinchona Alkaloid Derivatives as Highly Efficient Bifunctional Organocatalysts for the Asymmetric Addition of Malonate to Nitroalkenes: Inversion of Configuration at C9 Dramatically Improves Catalyst Performance," Angew. Chem. Int. Ed., 44:6367-6370 (2005).
Song, J. et al., "The Mannich Reaction of Malonates with Simple Imines Catalyzed by Bifunctional Cinchona Alkaloids: Enantioselective Synthesis of β-Amino Acids," J. Am. Chem. Soc., 128(18):6048-6049 (2006).
Tian, S-K. et al., "Asymmetric Organic Catalysis with Modified Cinchona Alkaloids," Acc. Chem. Res., 37(8):621-631(2004).
Vakulya, B. et al., "Highly Enantioselective Conjugate Addition of Nitromethane to Chalcones Using Bifunctional Cinchona Organocatalysts," Org. Lett., 7(10):1967-1969 (2005).
Wynberg, H. et al., "Asymmetric Catalysis by Alkaloids," Top. Sterochem., 16:87-129 (1986).

* cited by examiner

*Primary Examiner* — Daniel Sullivan
*Assistant Examiner* — Clinton Brooks
(74) *Attorney, Agent, or Firm* — Foley Hoag LLP

(57) ABSTRACT

The instability of carbamate-protected alkyl imines has greatly hampered the development of catalytic asymmetric Mannich reactions suitable for the synthesis of optically active carbamate-protected chiral alkyl amines. A highly enantioselective Mannich reaction with in situ generation of carbamate-protected imines from stable α-amido sulfones catalyzed by an organic catalyst has been developed. This reaction provides a concise and highly enantioselective route converting aromatic and aliphatic aldehydes into optically active aryl and alkyl β-amino acids.

29 Claims, 3 Drawing Sheets

DHQ-CLB

DHQD-CLB

DHQ-MEQ

DHQD-MEQ

DHQ-AQN

DHQD-AQN

DHQ-PHN

DHQD-PHN

*quinidine-based catalysts*

| Catalyst | R |
|---|---|
| QD-PH |  |
| QD-AN |  |
| QD-NT |  |
| QD-AC |  |
| QD-CH |  |

# CINCHONA ALKALOID-CATALYZED ASYMMETRIC MANNICH REACTIONS

RELATED APPLICATIONS

This application claims the benefit of priority to U.S. Provisional Patent Application Ser. No. 60/875,900, filed Dec. 20, 2006; the entirety of which is hereby incorporated by reference.

GOVERNMENT SUPPORT

This invention was made with government support under Grant No. GM61591 awarded by the National Institutes of Health. The government has certain rights in the invention.

BACKGROUND OF THE INVENTION

Catalytic enantioselective Mannich reactions provide one of the most versatile and attractive approaches for the generation of optically active chiral amines. Reviews: (a) Marques, M. M. B. *Angew. Chem., Int. Ed.* 2006, 45, 348. (b) Shibasaki, M.; Matsunaga, S. *J. Organomet. Chem.* 2006, 691, 2089. (c) Cordova, A. *Acc. Chem. Res.* 2004, 37, 102. (d) Kobayashi, S.; Ueno, M. In Comprehensive Asymmetric Catalysis Supplement I; Jacobsen, E. N., Pfaltz, A., Yamamoto, H., Eds.; Springer: Berlin, 2003 Chapter 29.5.

While great strides have been made over the last several years with both chiral metal and organic catalysts, only a few catalytic asymmetric Mannich reactions include both carbamate-protected aryl and alkyl imines as substrates. For recent reports of catalytic asymmetric Mannich reactions catalyzed by chiral metal-complexes, see (a) Sasamoto, N.; Dubs, C.; Hamashima, Y.; Sodeoka, M. *J. Am. Chem. Soc.* 2006, 128, 14010. (b) Trost, B. M.; Jaratjaroonphong, J.; Reutrakul, V. *J. Am. Chem. Soc.* 2006, 128, 2778. (c) Ihori, Y.; Yamashita, Y.; Ishitani, H.; Kobayashi, S. *J. Am. Chem. Soc.* 2005, 127, 15528. (d) Harada, S.; Handa, S.; Matsunaga, S.; Shibasaki, M. *Angew. Chem. Int. Ed.* 2005, 44, 4365. (e) Hamashima, Y.; Sasamoto, N.; Hotta, D.; Somei, H.; Umebayashi, N.; Sodeoka, M. *Angew. Chem. Int. Ed.* 2005, 44, 1525. (f) Kobayashi, S.; Ueno, M.; Saito, S.; Mizuki, Y.; Ishitani, H.; Yamashita, Y. *Proc. Natl. Acad. Sci. USA* 2004, 101, 5476. (g) Akiyama, T.; Itoh, J.; Yokota, K.; Fuchibe, K. *Angew. Chem. Int. Ed.* 2004, 43, 1566. (h) Josephsohn, N. S.; Snapper, M. L.; Hoveyda, A. H. *J. Am. Chem. Soc.* 2004, 126, 3734. (i) Marigo, M.; Kjærsgaard, A.; Juhl, K.; Gathergood, N.; Jørgensen, K. A. *Chem. Eur. J.* 2003, 9, 2359. (j) Natsunnga, S.; Kumagai, N.; Harada, S.; Shibasaki, M. *J. Am. Chem. Soc.* 2003, 125, 4712. (k) Kobayashi, S.; Matsubara, R.; Nakamura, Y.; Kitagawa, H.; Sugiura, M. *J. Am. Chem. Soc.* 2003, 125, 2507. (l) Bernardi, L; Gothelf, a. Hazell, R. Jørgensen, K. A. *J. Org. Chem.,* 2003, 68, 2583 (m) Trost, B. Terrell, L. R. *J. Am. Chem. Soc.* 2003, 125, 338. (n) Kobayashi, S.; Hamada, T.; Manabe, K. *J. Am. Chem. Soc.* 2002, 124, 5640. For recent reports of asymmetric Mannich reactions catalyzed by chiral organic catalysts, see (a) Zhang, H. L.; Mifsud, M.; Tanaka, F.; Barbas, III, C. F. *J. Am. Chem. Soc.* 2006, 128, 9630. (b) Song, J.; Wang, Y.; Deng, L. *J. Am. Chem. Soc.* 2006, 128, 6048. (c) Tillman, A. L.; Ye, J.; Dixon, D. *J. Chem. Commun.* 2006, 1191. (d) Ting, A.; Lou, S.; Schaus S. E. *Org. Let.* 2006, 8, 2003. (e) Mitsumori, S.; Zhang H.; Cheong, P. H.; Houk, K. N.; Tanaka, F.; Barbas, C. F., III. *J. Am. Chem. Soc.* 2006, 128, 1040. (f) Kano, T.; Yamaguchi, Y.; Tokuda, O.; Maruoka, K. *J. Am. Chem. Soc.* 2005, 127, 16408. (g) Lou, S.; Taoka, B. M.; Ting, A.; Schaus, S. E. *J. Am. Chem. Soc.* 2005, 127, 11256. (h) Poulsen T. B.; Alemparte, C.; Saaby, S.; Bella, M.; Jorgensen, K. A. *Angew. Chem. Int. Ed.* 2005, 44, 2896 (i) Uraguchi, D.; Terada, M. *J. Am. Chem. Soc.* 2004, 126, 5356. (j) Notz, W.; Tanaka, F.; Barbas III, C. F. *Acc. Chem. Res.* 2004, 37, 5801. (k) Zhuang, W.; Saaby, S.; Jørgensen, K. A. *Angew. Chem. Int. Ed.* 2004, 43, 4476 (l) Córdova, A. *Chem. Eur. J.* 2004, 10, 1987. (m) Notz, W.; Watanabe, S.-I.; Chowdari, N. S.; Zhong, G.; Betancort, J. M.; Tanaka, F.; Barbas, III, C. F. *Adv. Synth. Catal.* 2004, 346, 1131. (n) Hayashi, Y.; Tsuboi, W.; Ashimine, I.; Urushima, T.; Shoji, M.; Sakai, K. *Angew. Chem. Int. Ed.* 2003, 42, 3677. (o) Wenzel, A. G.; Lalonde, M. P.; Jacobsen, E. N. *Synlett* 2003, 1919. (p) Wenzel, A. G.; Jacobsen, E. N. *J. Am. Chem. Soc.* 2002, 124, 12964. (q) List B.; Pojarliev, P.; Biller, W. T.; Martin, H. J. *J. Am. Chem. Soc.* 2002, 124, 827. (r) List, B. *J. Am. Chem. Soc.* 2000, 122, 9336. For an asymmetric Mannich reaction catalyzed by a phase transfer catalyst, Okada, A.; Shibuguchi, T.; Ohshima, T.; Masu, H.; Yamaguchi, K.; Shibasaki, M. *Angew Chem., Int. Ed.* 2005, 44, 4564.

Palomo and the group of Herrera, Bernardi and Ricci independently reported highly enantioselective aza-Henry reactions with in situ generation of carbamate-protected aryl and alkyl imines from α-amido sulfones 1A promoted with a chiral phase transfer catalyst, thereby establishing asymmetric Mannich reactions tranforming directly the stable α-amido sulfones 1 into the corresponding aza-Henry (Mannich) adducts. Palomo, C.; Oiarbide, M.; Laso, A.; Lopez, R. *J. Am. Chem. Soc.* 2005, 127, 17622; and Fini, F.; Sgarzani, V.; Pettersen, D.; Herrera, R. P.; Bernardi, L.; Ricci, A. *Angew. Chem., Int. Ed.* 2005, 44, 7975. For a comprehensive review of using α-amido sulfones as stable precursors of N-acylimino derivatives, see Petrini, M. *Chem. Rev.* 2005, 105, 3949.

SUMMARY OF THE INVENTION

One aspect of the present invention relates to a method of forming a chiral non-racemic amine, comprising the step of: combining a nucleophile, a base, a chiral non-racemic catalyst, and a substrate selected from the group consisting of N-acyl imine, N-alkoxycarbonyl imine, N-aryloxycarbonyl imine, N-alkenyloxycarbonyl imine, N-aralkoxycarbonyl imine, N-aralkenyloxycarbonyl imine, N-alkylaminocarbonyl imine, N-arylaminocarbonyl imine, N-aralkylaminocarbonyl imine, N-aminocarbonyl imine, N-alkenylaminocarbonyl imine, N-aralkenylaminocarbonyl imine, N-alkylthiocarbonyl imine, N-arylthiocarbonyl imine, N-aryloxythiocarbonyl imine, N-alkoxythiocarbonyl imine, N-aralkoxythiocarbonyl imine, N-arylaminothiocarbonyl imine, N-aralkylaminothiocarbonyl imine, N-alkenyloxythiocarbonyl imine, N-alkenylaminothiocarbonyl imine, N-aminothiocarbonyl imine, N-alkylaminothiocarbonyl imine, N-aralkenyloxythiocarbonyl imine, N-aralkenylaminothiocarbonyl imine, N-alkylsulfonyl imine, N-arylsulfonyl imine, N-aralkylsulfonyl imine, N-alkenylsulforyl imine, N-arylphosphoryl imine, N-aralkylphosphoryl imine, N-alkenylphosphoryl imine and N-alkylphosphoryl imine; wherein said chiral non-racemic catalyst is a tertiary amine, phosphine or arsine; and said chiral non-racemic catalyst catalyzes the addition of said nucleophile to said substrate to give a chiral non-racemic amine.

In certain embodiments, the present invention relates to the aforementioned method, wherein said substrate is an N-alkoxycarbonyl imine, N-aryloxycarbonyl imine, N-alkenyloxycarbonyl imine, N-aralkoxycarbonyl imine or N-aralkenyloxycarbonyl imine.

In certain embodiments, the present invention relates to the aforementioned method, wherein said substrate is an N-alkoxycarbonyl imine, N-alkenyloxycarbonyl imine or N-aralkoxycarbonyl imine.

In certain embodiments, the present invention relates to the aforementioned method, wherein said substrate is an N-allyloxycarbonyl imine, N-benzyloxycarbonyl imine, N-tert-butoxycarbonyl imine, N-2,2,2-trichloroethoxycarbonyl imine, 2-(trimethylsilyl)ethoxycarbonyl imine or N-9-fluorenylmethoxycarbonyl imine.

In certain embodiments, the present invention relates to the aforementioned method, further comprising: combining an N-α-phosphonylalkyl O-alkyl carbamate, N-α-sulfonylalkyl O-alkyl carbamate, N-α-haloalkyl O-alkyl carbamate, N-α-phosphonylalkyl O-aryl carbamate, N-α-sulfonylalkyl O-aryl carbamate, N-α-haloalkyl O-aryl carbamate, N-α-phosphonylalkyl O-alkenyl carbamate, N-α-sulfonylalkyl O-alkenyl carbamate, N-α-haloalkyl O-alkenyl carbamate, N-α-phosphonylalkyl O-aralkyl carbamate, N-α-sulfonylalkyl O-aralkyl carbamate, N-α-haloalkyl O-aralkyl carbamate, N-α-phosphonylalkyl O-aralkenyl carbamate, N-α-sulfonylalkyl O-aralkenyl carbamate, or N-α-haloalkyl O-aralkenyl carbamate, and a base to generate an N-alkoxycarbonyl imine, N-aryloxycarbonyl imine, N-alkenyloxycarbonyl imine, N-aralkoxycarbonyl imine, or N-aralkenyloxycarbonyl imine.

In certain embodiments, the present invention relates to the aforementioned method, further comprising: combining an N-α-sulfonylalkyl O-alkyl carbamate, N-α-sulfonylalkyl O-aryl carbamate, N-α-sulfonylalkyl O-alkenyl carbamate, N-α-sulfonylalkyl O-aralkyl carbamate, or N-α-sulfonylalkyl O-aralkenyl carbamate, and a base to generate an N-alkoxycarbonyl imine, N-aryloxycarbonyl imine, N-alkenyloxycarbonyl imine, N-aralkoxycarbonyl imine, or N-aralkenyloxycarbonyl imine.

In certain embodiments, the present invention relates to the aforementioned method, wherein said nucleophile is selected from the group consisting of malonate, keto ester, nitroalkane, arylnitroalkane, cycloalkylnitroalkane and heterocyclicnitroalkane.

In certain embodiments, the present invention relates to the aforementioned method, wherein said nucleophile is a malonate.

In certain embodiments, the present invention relates to the aforementioned method, wherein said chiral non-racemic catalyst is a tertiary amine.

In certain embodiments, the present invention relates to the aforementioned method, wherein said chiral non-racemic catalyst is a cinchona alkaloid.

In certain embodiments, the present invention relates to the aforementioned method, wherein said chiral non-racemic catalyst is quinidine, (DHQ)₂PHAL, (DHQD)₂PHAL, (DHQ)₂PYR, (DHQD)₂PYR, (DHQ)₂AQN, (DHQD)₂AQN, DHQ-CLB, DHQD-CLB, DHQ-MEQ, DHQD-MEQ, DHQ-AQN, DHQD-AQN, DHQ-PHN, DHQD-PHN, QD-PH, QD-AN, QD-NT, QD-AC, QD-CH, QD-IP, QD-(−)-MN, QD-AD, Q-PH, Q-AN, Q-NT, Q-CH, Q-AC, Q-IP, Q-(−)-MN, Q-AD, 9-thiourea Q or 9-thiourea QD.

In certain embodiments, the present invention relates to the aforementioned method, wherein said chiral non-racemic catalyst is 9-thiourea Q or 9-thiourea QD.

In certain embodiments, the present invention relates to the aforementioned method, wherein said chiral non-racemic catalyst is represented by QD or Q:

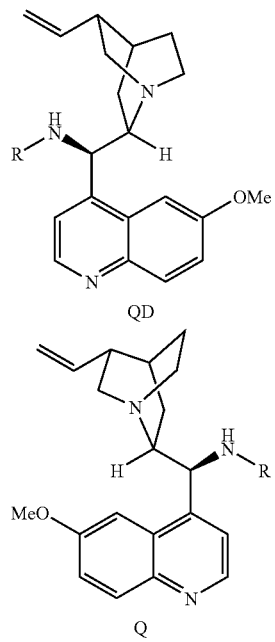

wherein

R represents hydrogen, alkyl, aryl, acyl, alkynyl, heteroaryl, cycloalkyl, cycloalkenyl, aralkyl, heteroaralkyl, heteroalkyl, alkoxycarbonyl, aryloxycarbonyl, alkenyloxycarbonyl, aralkoxycarbonyl, aralkenyloxycarbonyl, alkylaminocarbonyl, arylaminocarbonyl, aralkylaminocarbonyl, aminocarbonyl, alkenylaminocarbonyl, aralkenylaminocarbonyl, alkylthiocarbonyl, arylthiocarbonyl, aryloxythiocarbonyl, alkoxythiocarbonyl, aralkoxythiocarbonyl, arylaminothiocarbonyl, aralkylaminothiocarbonyl, alkenyloxythiocarbonyl, alkenylaminothiocarbonyl, aminothiocarbonyl, alkylaminothiocarbonyl, aralkenyloxythiocarbonyl, aralkenylaminothiocarbonyl, alkylsulfonyl, arylsulfonyl, aralkylsulfonyl, alkenylsulforyl, arylphosphoryl, aralkylphosphoryl, alkenylphosphoryl or alkylphosphoryl. In certain embodiments, the present invention relates to the aforementioned method, wherein R is arylaminothiocarbonyl. In certain embodiments, the present invention relates to the aforementioned method, wherein R is 3,5-bis(trifluoromethyl)phenylaminothiocarbonyl.

In certain embodiments, the present invention relates to the aforementioned method, wherein said base is a hydride, carbonate, phosphate, alkoxide, amide, hydroxide, or an organic base.

In certain embodiments, the present invention relates to the aforementioned method, wherein said base is an organic base.

In certain embodiments, the present invention relates to the aforementioned method, wherein said organic base is 2,6-lutidine, proton sponge or pempidine.

In certain embodiments, the present invention relates to the aforementioned method, wherein said base is a hydroxide.

In certain embodiments, the present invention relates to the aforementioned method, wherein said substrate is an N-alkoxycarbonyl imine, N-alkenyloxycarbonyl imine or N-aralkoxycarbonyl imine; and said nucleophile is a malonate.

In certain embodiments, the present invention relates to the aforementioned method, wherein said substrate is an N-alkoxycarbonyl imine, N-alkenyloxycarbonyl imine or N-aralkoxycarbonyl imine; and said nucleophile is a malonate; and said base is a hydroxide.

In certain embodiments, the present invention relates to the aforementioned method, wherein said substrate is an N-alkoxycarbonyl imine, N-alkenyloxycarbonyl imine or N-aralkoxycarbonyl imine; and said nucleophile is a malonate; and said base is a hydroxide; and said chiral non-racemic catalyst is a cinchona alkaloid.

In certain embodiments, the present invention relates to the aforementioned method, wherein said substrate is an N-alkoxycarbonyl imine, N-alkenyloxycarbonyl imine or N-aralkoxycarbonyl imine; and said nucleophile is a malonate; and said base is a hydroxide; and said chiral non-racemic catalyst is quinidine, (DHQ)$_2$PHAL, (DHQD)$_2$PHAL, (DHQ)$_2$PYR, (DHQD)$_2$PYR, (DHQ)$_2$AQN, (DHQD)$_2$AQN, DHQ-CLB, DHQD-CLB, DHQ-MEQ, DHQD-MEQ, DHQ-AQN, DHQD-AQN, DHQ-PHN, DHQD-PHN, QD-PH, QD-AN, QD-NT, QD-AC, QD-CH, QD-IP, QD-(−)-MN, QD-AD, Q-PH, Q-AN, Q-NT, Q-CH, Q-AC, Q-IP, Q-(−)-MN, Q-AD, 9-thiourea Q or 9-thiourea QD.

In certain embodiments, the present invention relates to the aforementioned method, wherein said substrate is an N-alkoxycarbonyl imine, N-alkenyloxycarbonyl imine or N-aralkoxycarbonyl imine; and said nucleophile is a malonate; and said base is a hydroxide; and said chiral non-racemic catalyst is 9-thiourea Q or 9-thiourea QD.

Another aspect of the present invention relates to a method of preparing a chiral non-racemic amine represented by Scheme 1:

Scheme 1

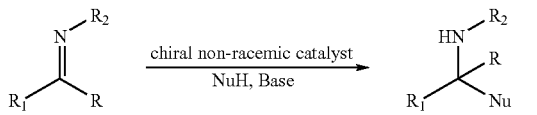

wherein said chiral non-racemic catalyst is a tertiary amine, phosphine or arsine;

R represents hydrogen, alkyl, aryl, heteroaryl, cycloalkyl, aralkyl, or heteroaralkyl;

$R_1$ represents alkyl, aryl, heteroaryl, cycloalkyl, aralkyl, or heteroaralkyl;

R and $R_1$, taken together, may form an optionally substituted ring consisting of 3-10 backbone atoms inclusive; said ring optionally comprising one or more heteroatoms;

$R_1$ and $R_2$, taken together, may form an optionally substituted ring consisting of 4-10 backbone atoms inclusive; said ring optionally comprising one or more heteroatoms beyond the nitrogen to which $R_2$ is bonded;

$R_2$ represents N-acyl, N-alkoxycarbonyl, N-aryloxycarbonyl, N-alkenyloxycarbonyl, N-aralkoxycarbonyl, N-aralkenyloxycarbonyl, N-alkylaminocarbonyl, N-arylaminocarbonyl, N-aralkylaminocarbonyl, N-aminocarbonyl, N-alkenylaminocarbonyl, N-aralkenylaminocarbonyl, N-alkylthiocarbonyl, N-arylthiocarbonyl, N-aryloxythiocarbonyl, N-alkoxythiocarbonyl, N-aralkoxythiocarbonyl, N-arylaminothiocarbonyl, N-aralkylaminothiocarbonyl, N-alkenyloxythiocarbonyl, N-alkenylaminothiocarbonyl, N-aminothiocarbonyl, N-alkylaminothiocarbonyl, N-aralkenyloxythiocarbonyl, N-aralkenylaminothiocarbonyl, N-alkylsulfonyl, N-arylsulfonyl, N-aralkylsulfonyl, N-alkenylsulfonyl, N-arylphosphoryl, N-aralkylphosphoryl, N-alkenylphosphoryl or N-alkylphosphoryl;

NuH represents malonate, keto ester, nitroalkane, arylnitroalkane, cycloalkylnitroalkane or heterocyclicnitroalkane; and base represents hydride, carbonate, phosphate, alkoxide, amide, hydroxide or an organic base.

In certain embodiments, the present invention relates to the aforementioned method, wherein $R_2$ represents alkoxycarbonyl, alkenyloxycarbonyl or aralkoxycarbonyl.

In certain embodiments, the present invention relates to the aforementioned method, wherein NuH represents malonate.

In certain embodiments, the present invention relates to the aforementioned method, wherein base represents hydroxide.

In certain embodiments, the present invention relates to the aforementioned method, wherein $R_2$ represents alkoxycarbonyl, alkenyloxycarbonyl or aralkoxycarbonyl; and NuH represents malonate.

In certain embodiments, the present invention relates to the aforementioned method, wherein $R_2$ represents alkoxycarbonyl, alkenyloxycarbonyl or aralkoxycarbonyl; and NuH represents malonate; and base represents hydroxide.

In certain embodiments, the present invention relates to the aforementioned method, wherein said chiral non-racemic catalyst is represented by QD or Q:

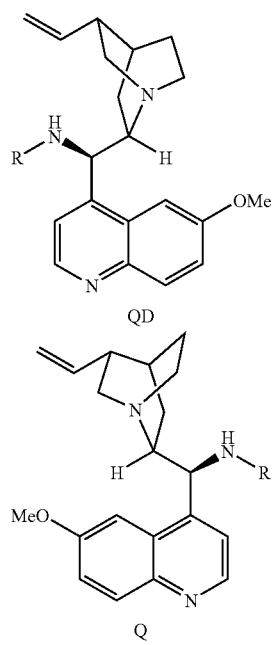

wherein

R represents hydrogen, alkyl, aryl, acyl, alkynyl, heteroaryl, cycloalkyl, cycloalkenyl, aralkyl, heteroaralkyl, heteroalkyl, alkoxycarbonyl, aryloxycarbonyl, alkenyloxycarbonyl, aralkoxycarbonyl, aralkenyloxycarbonyl, alkylaminocarbonyl, arylaminocarbonyl, aralkylaminocarbonyl, aminocarbonyl, alkenylaminocarbonyl, aralkenylaminocarbonyl, alkylthiocarbonyl, arylthiocarbonyl, aryloxythiocarbonyl, alkoxythiocarbonyl, aralkoxythiocarbonyl, arylaminothiocarbonyl, aralkylaminothiocarbonyl, alkenyloxythiocarbonyl, alkenylaminothiocarbonyl, aminothiocarbonyl, alkylaminothiocarbonyl, aralkenyloxythiocarbonyl, aralkenylaminothiocarbonyl, alkylsulfonyl, arylsulfonyl, aralkylsulfonyl, alkenylsulfonyl, arylphosphoryl, aralkylphosphoryl, alkenylphosphoryl or alkylphosphoryl. In certain embodiments, the present invention relates to the aforementioned method, wherein R is arylaminothiocarbonyl. In certain embodiments, the present invention relates to the aforementioned method, wherein R is 3,5-bis(trifluoromethyl)phenylaminothiocarbonyl.

In certain embodiments, the present invention relates to any of the aforementioned methods, wherein the enantiomeric excess or diastereomeric excess of the chiral non-racemic amine is greater than about 50%.

In certain embodiments, the present invention relates to any of the aforementioned methods, wherein the enantiomeric excess or diastereomeric excess of the chiral non-racemic amine is greater than about 70%.

In certain embodiments, the present invention relates to any of the aforementioned methods, wherein the enantiomeric excess or diastereomeric excess of the chiral non-racemic amine is greater than about 90%.

DETAILED DESCRIPTION OF THE INVENTION

Definitions

Figure 1:
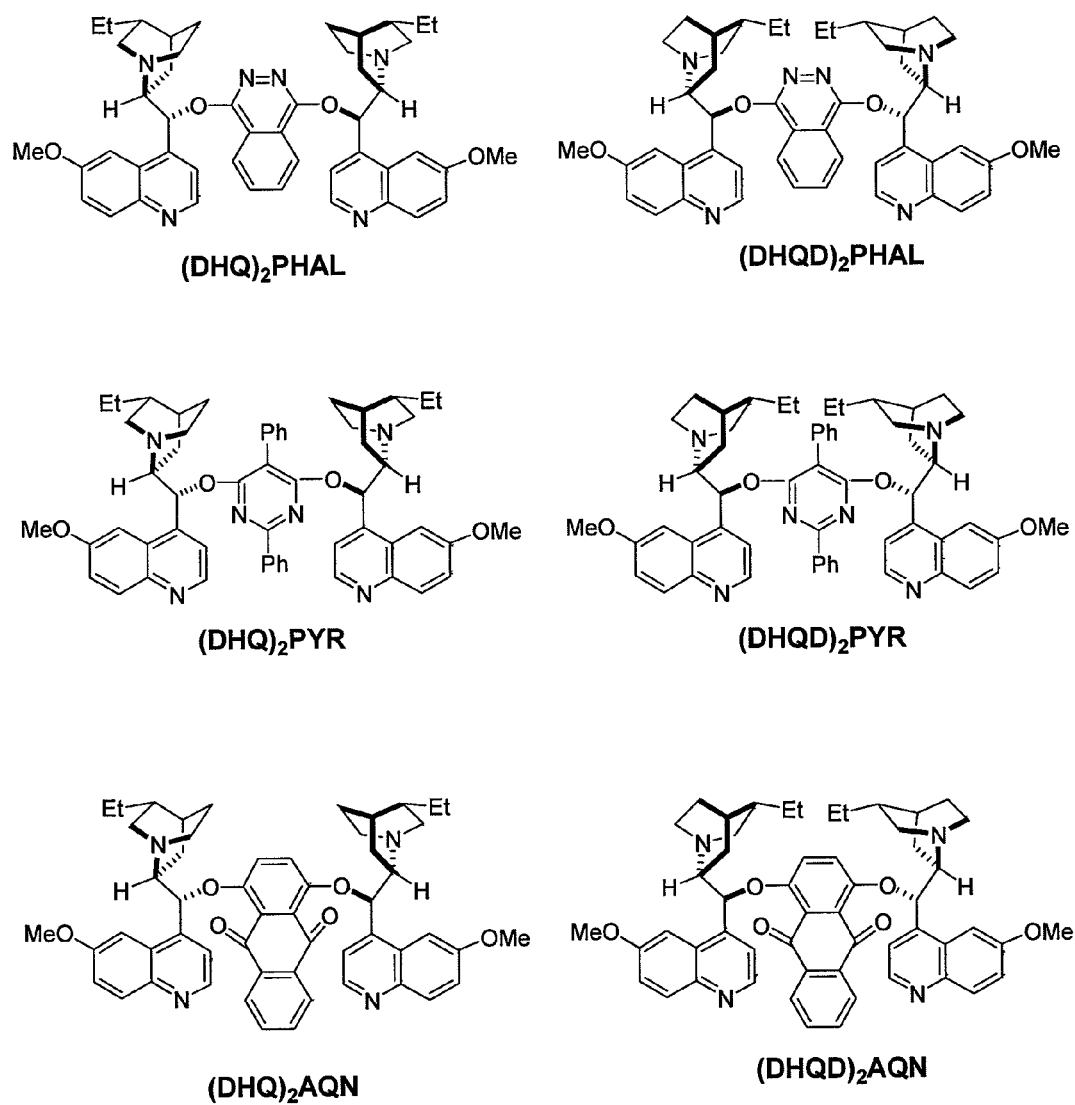
FIG. 1 depicts the structures of certain catalysts used in the methods of the present invention, and their abbreviations herein.
Figure 2:
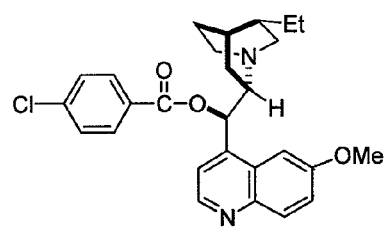
FIG. 2 depicts the structures of certain catalysts used in the methods of the present invention, and their abbreviations herein.
Figure 2:
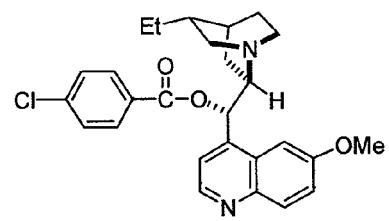
Figure 2:
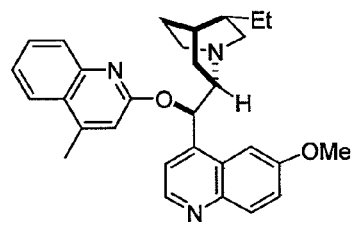
Figure 2:
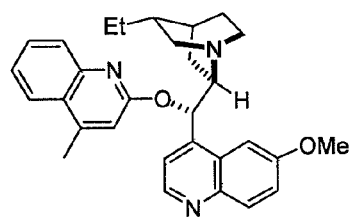
Figure 2:
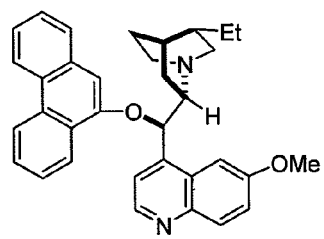
Figure 2:
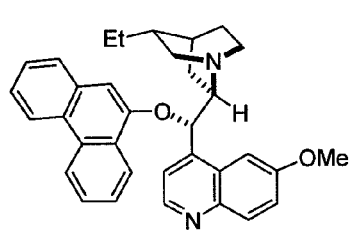
Figure 2:
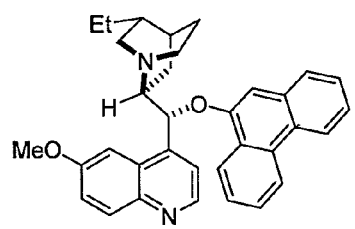
Figure 2:
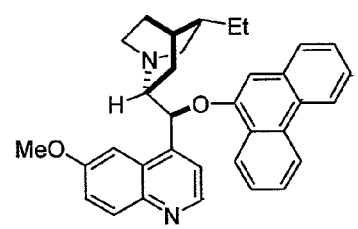
Figure 3:
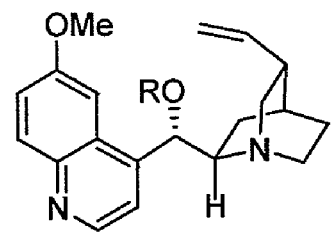
FIG. 3 depicts the structures of QD-PH, QD-AN, QD-NT, QD-AC and QD-CH.
Figure 3:
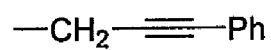
Figure 3:
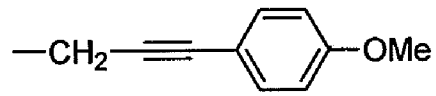
Figure 3:
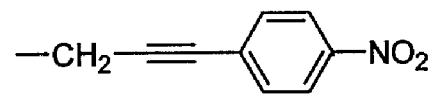
Figure 3:
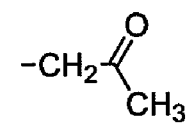
Figure 3:
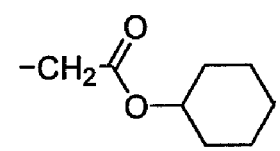

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A$ ($ee$)=(% Enantiomer $A$)−(% Enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

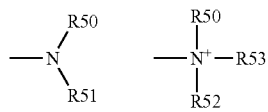

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

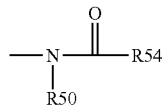

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

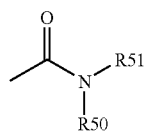

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C═O)NRR', where R and R' are independently H, aliphatic groups, aryl groups or heteroaryl groups.

The term "oxo" refers to a carbonyl oxygen (═O).

The terms "oxime" and "oxime ether" are art-recognized and refer to moieties that may be represented by the general formula:

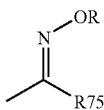

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

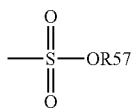

in which R57 is an electron pair, hydrogen, alkyl, cycloalkyl, or aryl.

The term "sulfate" is art recognized and includes a moiety that may be represented by the general formula:

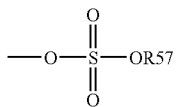

in which R57 is as defined above.

The term "sulfonamido" is art recognized and includes a moiety that may be represented by the general formula:

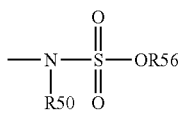

in which R50 and R56 are as defined above.

The term "sulfamoyl" is art-recognized and refers to a moiety that may be represented by the general formula:

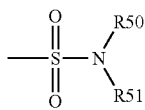

in which R50 and R51 are as defined above.

The term "sulfonyl" is art-recognized and refers to a moiety that may be represented by the general formula:

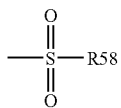

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

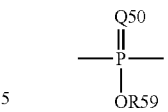

wherein Q50 represents S or O, and R59 represents hydrogen, a lower alkyl or an aryl. When used to substitute, e.g., an alkyl, the phosphoryl group of the phosphorylalkyl may be represented by the general formulas:

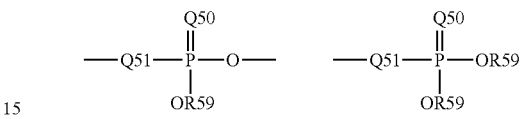

wherein Q50 and R59, each independently, are defined above, and Q51 represents O, S or N. When Q50 is S, the phosphoryl moiety is a "phosphorothioate".

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

The term "1-adamantyl" is art-recognized and includes a moiety represented by the formula:

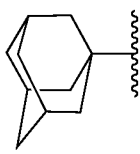

The term "(−)-menthyl" is art-recognized and includes a moiety represented by the formula:

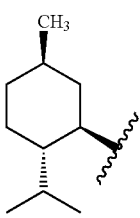

The term "(+)-menthyl" is art-recognized and includes a moiety represented by the formula:

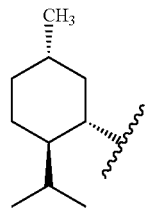

The term "isobornyl" is art-recognized and includes a moiety represented by the formula:

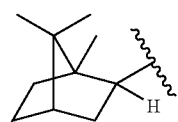

The term "isopinocamphyl" is art-recognized and includes a moiety represented by the formula:

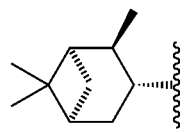

The term "(+)-fenchyl" is art-recognized and includes a moiety represented by the formula:

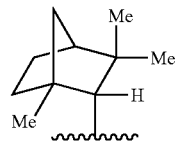

The term "QD" is represented by the formula:

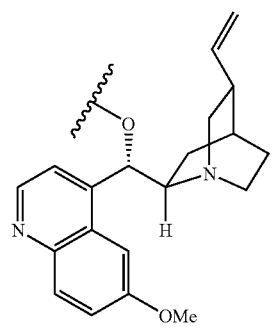

The term "Q" is represented by the formula:

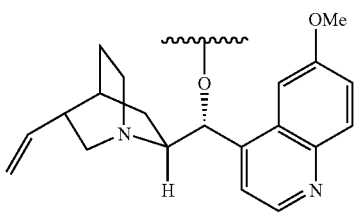

Reaction Conditions

The asymmetric reactions of the present invention may be performed under a wide range of conditions, though it will be understood that the solvents and temperature ranges recited herein are not limitative.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

Exemplary Methods of the Invention

As precursors to carbamate-protected chiral alkyl amines, carbamate-protected alkyl imines constitute a particularly important class of imine substrates for asymmetric Mannich reactions. However, their instability render it extremely challenging to employ them in catalytic asymmetric Mannich reactions. Specifically, spontaneous tautomerization of N-Boc alkyl imines, such as 2Aa and 2Ab, into the corresponding enamines typically occurs readily even at −20° C. (Scheme 1). Furthermore, no procedure has been reported for the preparation of N-Cbz alkyl imines (2B) in pure form.

Scheme 1. Synthesis and Tautomerization of N-Carbamate Imines.

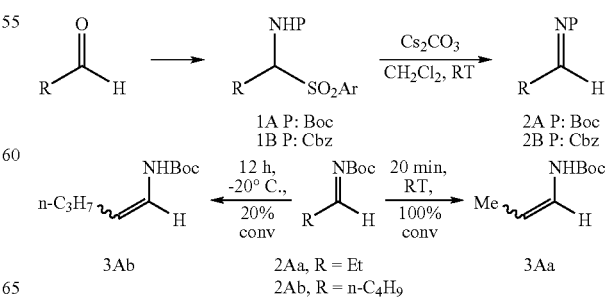

Remarkably, we have discovered an efficient, general and practical asymmetric Mannich reaction of imines bearing any one of a range of electron-withdrawing groups on the imine nitrogen, which is catalyzed by a bifunctional organic catalyst, wherein the imine may be generated in situ from a nitrogen-containing starting material bearing a leaving group alpha to the nitrogen. In certain embodiments, carbamate-protected imines 2, which may be generated from from α-amido sulfones 1, react with nucleophiles (e.g., malonates) under catalysis by a bifunctional organic catalyst (e.g., QD-4).

Recently, the 9-thiourea cinchona alkaloid 4 (FIG. 1) was identified independently by us and Dixon and workers as efficient catalysts for enantioselective additions of malonates and β-ketoesters to N-Boc aryl imines. Catalyst 4, accessible in two steps from quinine or quinidine, was reported independently by (a) Li, B.; Jiang, L.; Liu, M.; Chen, Y.; Ding, L.; Wu, Y. *Synlett* 2005, 4, 603 and (b) Vakulya, B.; Varga, S.; Csámpai, A.; Soós, T. *Org. Lett.* 2005, 7, 1967. For asymmetric reactions catalyzed by 4 see: (c) Wang, J.; Li, H.; Zu, L. Z.; Xie, H. X.; Duan, W. H.; Wang, W. *J. Am. Chem. Soc.* 2006, 128, 12652. (d) Wang, Y. Q.; Song, J.; Hong, R.; Deng, L. *J. Am. Chem. Soc.* 2006, 128, 8156. (e) Bernardi, L.; Fini, F.; Herrera, R. P.; Ricci, A.; Sagarzabu, V. *Tetrahedron,* 2006, 62, 375. (f) Mccooey, S. H.; Connon, S. J. *Angew. Chem., Int. Ed.* 2005, 44, 6367. (g) Ye, J.; Dixon, D. J.; Hynes, P. *Chem. Commun.* 2005, 35, 4481. We also demonstrated that 4 affords high enantioselectivity for the addition of malonates to N-Boc alkyl imines. The Mannich reaction of N-Boc phenyl imine 2Ac (R=Ph) and malonate 5 with 20 mol % of QD-4 afforded the desired Mannich adduct 6Ae in 74% ee at room temperature. Employing a stoichiometric amount of QD-4, 6Ac could be produced in 92% ee at room temperature. Alternatively, highly enantiomerically enriched 6Ac (97% ee) was obtained by performing the reaction at −60° C. for 36 hours with 20 mol % of QD-4. The reactions with N-Boc alkyl imines, such as 2Aa and 2Ab, afforded the Mannich adduct in useful optical purity and yield when performed with a stoichiometric loading of QD-4 at 0° C.

FIG. 1. Structures of two 9-Thiourea Cinchona Alkaloids

A Mannich reaction catalyzed by 4 with in situ generation of carbamate-protected imines 2 from the stable α-amido sulfones 1 would overcome these drawbacks (Scheme 2). It would eliminate the separate preparation of the carbamate-protected imines, thereby avoiding the need to prepare and handle the highly unstable carbamate-protected alkyl imines 2 (R=alkyl). Moreover, as the Mannich reactions with one equivalent of catalyst 4 were shown to convert both N-Boc aryl and alkyl imines 2A into the corresponding Mannich adducts 6 in high ee at room temperature, by maintaining a higher concentration of catalyst 4 relative to N-carbamate imines 2 via the gradual and in situ generation of 2, a room temperature Mannich reaction with catalyst 4 in low loading could furnish the Mannich adduct 6 in high optical purity.

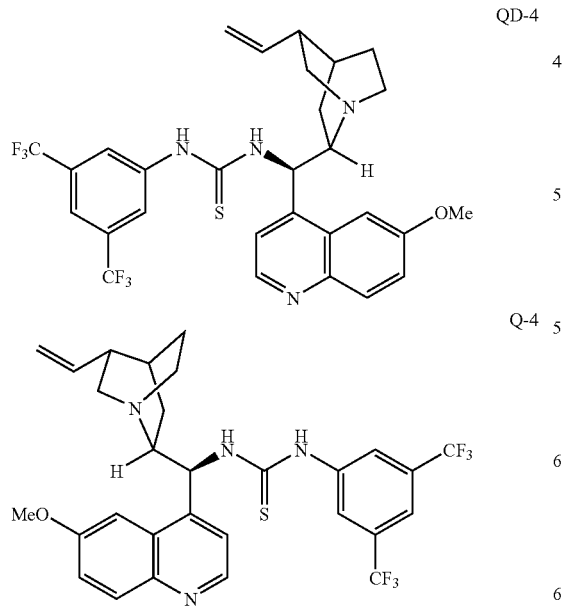

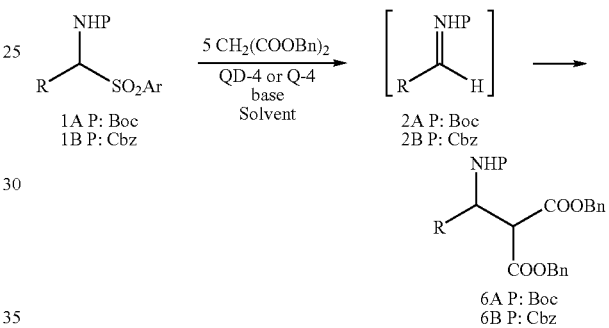

TABLE 1

Screening of Bases for Asymmetric Mannich Reactions with in situ Generation of Carbamate-Protected Imines Catalyzed by QD-4[a]

| entry | Base | Time/h | conversion/%[b] | ee/%[c] |
|---|---|---|---|---|
| 1 | Protonsponge | 3 | 14 | 35 |
| 2 | 2,6-Lutidine | 3 | 12 | 47 |
| 3 | Pempidine | 3 | 38 | 17 |
| 4 | $K_2CO_3$ (solids) | 3 | 33 | 81 |
| 5 | $Cs_2CO_3$ (solids) | 3 | 79 | 50 |
| 6 | $K_2CO_3$ (0.10 M) | 3 | 92 | 91 |
| 7 | $Cs_2CO_3$ (0.10 M) | 3 | 92 | 90 |

TABLE 1-continued

Screening of Bases for Asymmetric Mannich Reactions
with in situ Generation of Carbamate-Protected
Imines Catalyzed by QD-4[a]

| 8 | Na$_2$CO$_3$ (0.10 M) | 3 | 90 | 95 |
| 9 | NaOH (0.10 M) | 3 | 100 | 83 |
| 10 | KOH (0.10 M) | 3 | 88 | 83 |
| 11 | CsOH (0.10 M) | 3 | 80 | 82 |

[a]Unless noted, reactions were run with 1Ac (0.10 mmol) and dibenzyl malonate 5 (0.15 mmol) in methylene chloride (500 µl) with base (1.0 eq) in the prescence of QD-4 (20 mol %) at room temperature.
[b]Determined by $^1$H NMR analysis.
[c]Determined by HPLC.

Remarkably, with N-Boc amido sulfone 1Ac and benzyl malonate 5, the 4-catalyzed Mannich reaction with in situ generation of N-Boc phenyl imines 2Ac was examined with various amines and inorganic bases. As summarized in Table 1, promising results were obtained with several inorganic bases applied to the reaction as either a solid or an aqueous solution (entries 4-11, Table 1). In particular, at room temperature and promoted by 20 mol % of QD-4, the reaction employing a 0.1 M aqueous solution of Na$_2$CO$_3$ furnished the desired Mannich adduct 6Ac in 95% ee. In comparison, with the same loading of QD-4, a room temperature Mannich reaction utilizing the preformed N-Boc phenyl imine 2Ac afforded 6Ac in 74% ee. Further optimization studies established that an one-pot transformation of 1Ac to 6Ac in 89% yield and 96% ee could be achieved with 5.0 mol % of QD-4 at 0° C. (entry 11, Table 2).

TABLE 2

Reaction Condition Optimization[a]

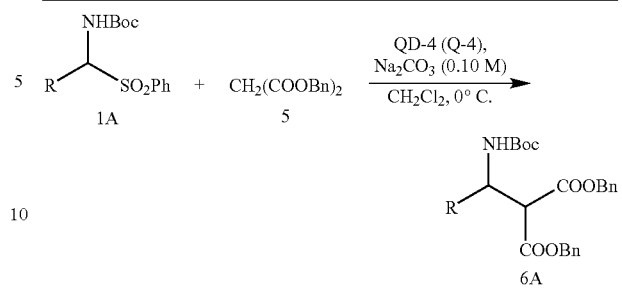

| entry | catalyst loading/% | solvent | temp/° C. | Time/h | conversation/%[b] | ee/%[c] |
|---|---|---|---|---|---|---|
| 1 | 20 | CH$_2$Cl$_2$ | RT | 3 | 90 | 95 |
| 2 | 20 | Acetone | RT | 3 | 100 | 74 |
| 3 | 20 | THF | RT | 3 | 100 | 20 |
| 4 | 20 | CHCl$_3$ | RT | 3 | 82 | 91 |
| 5 | 20 | EtOAc | RT | 3 | 100 | 76 |
| 6 | 20 | Toluene | RT | 3 | 47 | 89 |
| 8 | 10 | CH$_2$Cl$_2$ | RT | 5 | 100 | 68 |
| 9 | 10 | CH$_2$Cl$_2$ | 0° C. | 10 | 100 | 89 |
| 10[d] | 10 | CH$_2$Cl$_2$ | 0° C. | 10 | 100 | 96 |
| 11[d] | 5 | CH$_2$Cl$_2$ | 0° C. | 20 | 100 | 96 |

[a]Unless noted, reactions were run with 1Ac (0.10 mmol) and dibenzyl malonate 5 (0.15 mmol) in the solvent (500 µl) with base (1.0 eq) in the prescence of QD-4 (20 mol %) at room temperature.
[b]Determined by $^1$H NMR analysis.
[c]Determined by HPLC.
[d]Reaction was carried out in methylenen chloride (200 uL).

TABLE 3

Reactions of Malonate 5 with α-Amido Sulfones
Prepared from Aromatic and Heteroaromatic Aldehydes[a]

| entry | 1A | R | yield/%[b] | ee/%[c] |
|---|---|---|---|---|
| 1 | 1Ac | Ph- | 89(92) | 96(92) |
| 2 | 1Ad | 2-Me-Ph- | 96(91) | 95(90) |
| 3 | 1Ae | 3-Me-Ph- | 88(91[d]) | 95(88[d]) |
| 4 | 1Af | 4-Me-Ph- | 97(88) | 95(89) |
| 5 | 1Ag | 4-F-Ph- | 99(95) | 94(90) |
| 6 | 1Ah | 4-OMe-Ph | 90(87) | 95(90) |
| 7 | 1Ai | 2-furyl | 90(91) | 96(92) |
| 8 | 1Aj | 2-thienyl | 91(87[d]) | 94(85[d]) |

[a]Unless noted, reactions were run with 1A (0.525 mmol) and dibenzyl malonate 5 (0.50 mmol) in methylene chloride (1.0 mL) with sodium carbonate aqueous solution (0.10 M, 6.0 mL) in the prescence of QD-4 (5 mol %) at 0° C. for 20 h. The results in the parentheses were obtained with Q-4 (5 mol %) to give the opposite enantionmer.
[b]Isolated yield.
[c]Determined by HPLC.
[d]Reaction was run with Q-4 (10 mol %).

Importantly, the 4-catalyzed Mannich reactions starting with α-amido sulfones 1A, prepared from a broad range of aromatic and heteroaromatic aldehydes, furnished the corresponding Mannich adducts 6 in high ee and yield (Table 3). It is noteworthy that neither the position nor the electronic properties of the substituent on the aromatic ring was found to have a significant impact on the enantioselectivity of the reaction.

TABLE 4

Reactions of Malonate 5 with α-Amido Sulfones
Prepared from Aliphatic Aldehydes

TABLE 4-continued

Reactions of Malonate 5 with α-Amido Sulfones
Prepared from Aliphatic Aldehydes

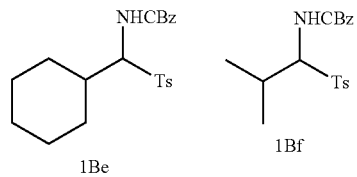

| entry | 1 | Base | Time/h | Yield/%[b] | ee/%[c] |
|---|---|---|---|---|---|
| 1[d,e] | 1Aa | Cs₂CO₃ | 24 | 45 | 88 |
| 2[d,e] | 1Ab | Cs₂CO₃ | 24 | 44 | 90 |
| 3 | 1Ba | CsOH | 20(72[f]) | 64(70) | 91(93[f]) |
| 4 | 1Bb | CsOH | 20(20[d]) | 78(75) | 93(91[d]) |
| 5 | 1Bc | CsOH | 20(72[d,f]) | 88(80) | 92(92[d,f]) |
| 6 | 1Bd | CsOH | 20(96[f]) | 70(67) | 85(82[f]) |
| 7[d] | 1Be | Cs₂CO₃ | 96(96) | 73(81) | 90(87) |
| 8[d] | 1Bf | Cs₂CO₃ | 96(96) | 67(70) | 85(82) |

[a]Unless noted, reactions were run with 1 (0.40 mmol) and dibenzyl malonate 5 (0.60 mmol) in methylene chloride (0.80 mL) with CsOH (0.10 M, 4.0 mL) or Cs₂CO₃ (0.10 M, 4.8 mL) in the prescence of QD-4 (10 mol %) at 0° C. The results in the parentheses were obtained with Q-4 (10 mol %) to give the opposite enantionmer.
[b]Isolated yields.
[c]Determined by HPLC.
[d]Reaction was carried out in methylene chloride (0.40 mL).
[e]Reaction was carried out at room temperature.
[f]Reaction was carried out in Cs₂CO₃ (1.2 eq) for 72-96 h.

We next focused on the 4-catalyzed Mannich reactions with in situ generation of the unstable carbamate-protected alkyl imines 2 (R=alkyl). Since the rates of both the in situ generation of the carbamate-protected alkyl imines and their consumption in the subsequent 4-catalyzed Mannich reactions differ significantly from those of carbamate-protected aryl imines, optimization studies were necessary for the identification of the optimal base for reactions starting with α-amido sulfones derived from aliphatic aldehydes. For reactions with N-Boc α-amido sulfones 1Aa and 1Ab, favorable results were obtained with aqueous Cs₂CO₃ (0.1 M) solution. With 10 mol % of QD-4 and at room temperature, the one-pot transformations of the α-amido sulfones 1Aa and 1Ab into the corresponding Mannich adducts 6Aa-6Ab were accomplished in 88 and 90% ee, respectively (entries 1-2, Table 4). The optically active Mannich adducts 6Aa-6Ab were obtained in 44-45% yield because a significant amount of the in situ generated N-Boc alkyl imines was found to undergo spontaneous tautomerization. Remarkably, we found that, with 0.1 M aqueous CsOH, direct transformations of N-Cbz α-amido sulfones 1Ba-1Bf, prepared from aliphatic aldehydes of a significant degree of steric variations, into the corresponding Mannich adducts 6Ba-6Bf could be achieved in good to excellent ee and 60-88% yield (entries 3-8, Table 4). These results represent a significant expansion of the scope of the 4-catalyzed Mannich reaction of malonates with carbamate-protected imines.

EXEMPLIFICATION

The invention now being generally described, it will be more readily understood by reference to the following examples which are included merely for purposes of illustration of certain aspects and embodiments of the present invention, and are not intended to limit the invention.

General Information

¹H and ¹³C NMR spectra were recorded on a Varian instrument (400 MHz and 100 MHz, respectively). ¹H spectra was internally referenced to tetramethylsilane signal and ¹³C NMR spectra was internally referenced to CDCl₃ signal (δ=77.0 ppm). Data for ¹H NMR are reported as follows: chemical shift (δ, ppm), multiplicity (s, singlet; d, doublet; t, triplet; q, quartet; m, multiplet), coupling constant (Hz) and integration. Data for ¹³C NMR are reported in terms of chemical shift (δ, ppm). Infrared spectra were recorded on a Perkin Elmer FT-IR Spectrometer and are reported in frequency of absorption (cm⁻¹). Low resolution mass spectra for all the new compounds were performed by 70SE CI+, and exact mass spectra were recorded on a 70-VSE-B high resolution mass spectrometer. Specific rotations were measured on a Jasco Digital Polarimeter.

High performance liquid chromatography (HPLC) analysis was performed on a Hewlett-Packard 1100 Series instrument equipped with a quaternary pump, using a Daicel Chiralcel OJ, OD Column (250×4.6 mm) or Chiralpak AD, AS Column (250×4.6 mm) or Regis Pirckle covalent (R, R) Whelk-O 1 Column (250×4.6 mm). All the columns are held in the Agilent 1100 series thermostatted column compartment. UV absorption was monitored at 220 nm.

Materials

Catalysts QD-4 and Q-4 were prepared according to literature procedures. Vakulya, B.; Varga, S.; Csámpai, A.; Soós, T. Org. Lett. 2005, 7, 1976.

N-Boc α-amido sulfones 1A were prepared according to literature procedures. Wenzel, A. G.; Jacobsen, E. N. J. Am. Chem. Soc. 2002, 124, 12964.

N-Cbz α-amido sulfones 1B were prepared according to literature procedures. Pearson, W.; Lindbeck, A.; Kampf, J. J. Am. Chem. Soc. 1993, 115, 2622.

Methylene chloride was distilled from calcium hydride under nitrogen atmosphere.

All the other reagents were used as received.

General Procedure for Enantionselective Mannich Reaction of Malonate 5 to N-Boc α-amido Sulphones 1A

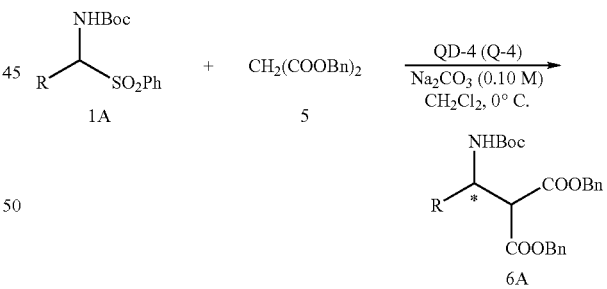

To a solution of N-Boc α-amido sulfones 1A (0.525 mmol, 1.05 equiv), dibenzylmalonate 5 (0.50 mmol, 1.0 equiv) and QD-4 or Q-4 (0.025 mmol, 5 mol %) in methylene chloride (1.0 mL) at 0° C., was added chilled sodium carbonate aqueous solution (0.10 M, 6.0 mL, 1.2 equiv) in one portion. The resulting biphasic reaction mixture was kept stirring at 0° C. for 20 h. Then the reaction mixture was diluted with water (10 mL) and extracted with ethyl ether (25 mL, three times). Organic layers were combined, washed with brine (30 mL), dried over anhydrous sodium sulfate and concentrated under reduced pressure. Crude product was purified by silica gel flash chromatography using the solvent specified below.

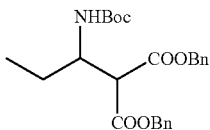

6Aa (+)-6Aa This product was obtained as a colorless oil (40 mg) in 45% yield after flash chromatography (Hexanes/Methylene chloride=1/1 to remove malonate, then eluent was changed to Hexanes/Ethyl Acetate=10/1) and in 88% ee as determined by HPLC [Daicel Chiralcel OD, Hexanes/IPA=98/2, 1.0 ml·min$^{-1}$, λ=220 nm, 20.0° C., $t_r$ (major)= 19.07 min, $t_r$ (minor)=17.32 min] from a reaction of N-Boc α-amido sulfones 1Aa (0.20 mmol, 1.0 equiv), dibenzylmalonate 5 (0.40 mmol, 2.0 equiv) and cesium carbonate (0.10M aqueous solution, 4.8 mL) in methylene chloride (0.20 mL) catalyzed by QD-4 (10 mol %) at room temperature for 24 h. The spectral characteristics were in agreement with those reported in the literature. Song, J.; Wang, Y.; Deng, L. *J. Am. Chem. Soc.* 2006, 128 (18), 6048-6049.

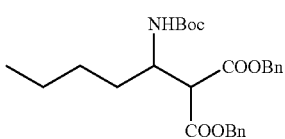

6Ab (+)-6Ab This product was obtained as a colorless oil (41 mg) in 44% yield after flash chromatography (silica gel: methylene chloride/Hexanes=1.5/1) and in 90% ee as determined by HPLC [Daicel Chiralcel OD, Hexanes IPA=98/2, 1.0 ml·min$^{-1}$, λ=220 nm, 20.0° C., $t_r$ (major)=14.63 min, $t_r$ (minor)=13.04 min] from a reaction of N-Boc α-amido sulfones 1Ab (0.20 mmol, 1.0 equiv), dibenzylmalonate 5 (0.40 mmol, 2.0 equiv) and cesium carbonate (0.10M aqueous solution, 4.8 mL) in methylene chloride (0.20 mL) catalyzed by QD-4 (10 mol %) at room temperature for 24 h. The spectral characteristics were in agreement with those reported in the literature.[4]

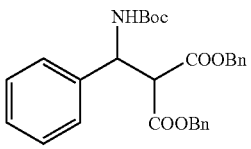

6Ac (+)-6Ac This product was obtained as a white solid (218 mg) in 89% yield after flash chromatography (silica gel: Ethyl acetate/Hexanes=1/10) and in 97% ee as determined by HPLC [Regis Pirckle Covalent (R, R) Whelk-O 1, Hexanes/IPA=95/5, 1.0 ml·min$^{-1}$, λ=220 nm, 20.0° C., $t_r$ (major)=12.63 min, $t_r$ (minor)=15.62 min] from a reaction catalyzed by QD-4 (5 mol %) at 0° C. for 20 h. The spectral characteristics were in agreement with those reported in the literature. Song, J.; Wang, Y.; Deng, L. *J. Am. Chem. Soc.* 2006, 128 (18), 6048-6049.
(−)-6Ac This product was obtained as a white solid in 92% yield and 92% ee from a reaction catalyzed by Q-4 (5 mol %) at 0° C. for 20 h.

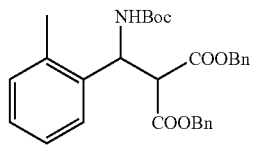

6Ad (+)-6Ad This product was obtained as a colorless oil (234 mg) in 96% yield after flash chromatography (silica gel: Ethyl acetate/Hexanes=1/10) and in 96% ee as determined by HPLC [Daicel chiralpak AS, Hexanes/IPA=95/5, 1.0 ml·min$^{-1}$, λ=220 nm, 20.0° C., $t_r$ (major)=12.07 min, $t_r$ (minor)=7.70 min] from a reaction catalyzed by QD-4 (5 mol %) at 0° C. for 20 h. The spectral characteristics were in agreement with those reported in the literature. Song, J.; Wang, Y.; Deng, L. *J. Am. Chem. Soc.* 2006, 128 (18), 6048-6049.
(−)-6Ac This product was obtained as a colorless oil in 91% yield and 90% ee from a reaction catalyzed by Q-4 (5 mol %) at 0° C. for 20 h.

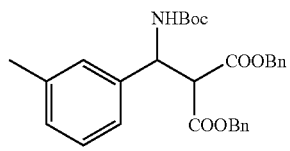

6Ae (+)-6Ae This product was obtained as a colorless oil (249 mg) in 88% yield after flash chromatography (silica gel: Ethyl acetate/Hexanes=1/12) and in 95% ee as determined by HPLC [Daicel Chiralcel OD, Hexanes/IPA=90:10, 1.0 ml·min$^{-1}$, λ=220 nm, 20.0° C., $t_r$ (major)=9.13 min, $t_r$ (minor)=7.65 min] from a reaction catalyzed by QD-4 (5 mol %) at 0° C. for 20 h. The spectral characteristics were in agreement with those reported in the literature. Song, J.; Wang, Y.; Deng, L. *J. Am. Chem. Soc.* 2006, 128 (18), 6048-6049.
(−)-6Ae This product was obtained as a colorless oil in 91% yield and 88% ee from a reaction catalyzed by Q-4 (10 mol %) at 0° C. for 20 h.

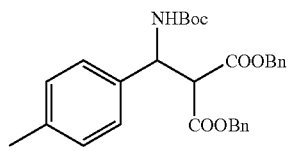

6Af yield after flash chromatography (silica gel: Ethyl acetate/Hexanes=1/8) and in 94% ee as determined by HPLC [Regis Pirckle Covalent (R, R) Whelk-O 1, Hexanes/IPA=98/2, 1.0 ml·min$^{-1}$, λ=220 nm, 20.0° C., $t_r$ (major)=22.65 min, $t_r$ (minor)=30.47 min] from a reaction catalyzed by QD-4 (5 mol %) at 0° C. for 20 h. The spectral characteristics were in agreement with those reported in the literature. Song, J.; Wang, Y.; Deng, L. *J. Am. Chem. Soc.* 2006, 128 (18), 6048-6049.
(−)-6Af This product was obtained as a colorless oil in 88% yield and 89% ee from a reaction catalyzed by Q-4 (5 mol %) at 0° C. for 20 h.

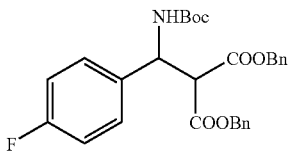

6Ag (+)-6Ag This product was obtained as a white solid (251 mg) in 99% yield after flash chromatography (silica gel: Ethyl acetate/Hexanes=1/8) and in 94% ee as determined by HPLC [Daicel Chiralcel OD, Hexanes/IPA=90:10, 1.0 ml·min$^{-1}$, λ=220 nm, 20.0° C., $t_r$ (major)=12.88 min, $t_r$ (minor)=9.60 min] from a reaction catalyzed by QD-4 (5 mol %) at 0° C. for 20 h. The spectral characteristics were in agreement with those reported in the literature. Song, J.; Wang, Y.; Deng, L. *J. Am. Chem. Soc.* 2006, 128 (18), 6048-6049.

(−)-6Ag This product was obtained as a white solid in 95% yield and 90% ee from a reaction catalyzed by Q-4 (5 mol %) at 0° C. for 20 h.

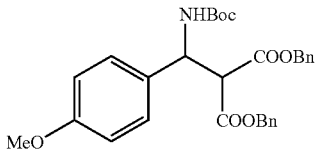

6Ah (+)-6Ah This product was obtained as a white solid (234 mg) in 90% yield after flash chromatography (silica gel: Ethyl acetate/Hexanes=1/10) and in 95% ee as determined by HPLC [Daicel Chiralcel OD, Hexanes IPA=90/10, 1.0 ml·min$^{-1}$, λ=220 nm, 20.0° C., $t_r$ (major)=14.68 min, $t_r$ (minor)=11.44 min] from a reaction catalyzed by QD-4 (5 mol %) at 0° C. for 36 h. The spectral characteristics were in agreement with those reported in the literature. Song, J.; Wang, Y.; Deng, L. *J. Am. Chem. Soc.* 2006, 128 (18), 6048-6049.

(−)-6Ah This product was obtained as a white solid in 87% yield and 90% ee from a reaction catalyzed by Q-4 (5 mol %) at 0° C. for 36 h.

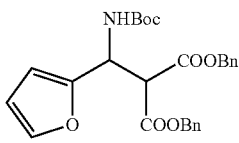

6Ai (+)-6Ai This product was obtained as a colorless oil (216 mg) in 90% yield after flash chromatography (silica gel: Ethyl acetate/Hexanes=1/12) and in 96% ee as determined by HPLC [Daicel Chiralpak AD, Hexanes/IPA=90/10, 1.0 ml·min$^{-1}$, λ=220 nm, 20.0° C., $t_r$ (major)=25.36 min, $t_r$ (minor)=32.15 min] from a reaction catalyzed by QD-4 (5 mol %) at 0° C. for 20 h. The spectral characteristics were in agreement with those reported in the literature. Song, J.; Wang, Y.; Deng, L. *J. Am. Chem. Soc.* 2006, 128 (18), 6048-6049.

(−)-6Ai This product was obtained as a colorless oil in 91% yield and 92% ee from a reaction catalyzed by Q-4 (5 mol %) at 0° C. for 20 h.

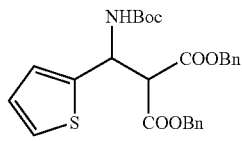

6Aj (+)-6Aj This product was obtained as a white solid (224 mg) in 91% yield after flash chromatography (silica gel: Ethyl acetate/Hexanes=1/20) and in 94% ee as determined by HPLC [Daicel Chiralcel OD, Hexanes/IPA=98/2, 1.0 ml·min$^{-1}$, λ=220 nm, 20.0° C., $t_r$ (major)=38.45 min, $t_r$ (minor)=33.02 min] from a reaction catalyzed by QD-4 (5 mol %) at 0° C. for 20 h. The spectral characteristics were in agreement with those reported in the literature. Song, J.; Wang, Y.; Deng, L. *J. Am. Chem. Soc.* 2006, 128 (18), 6048-6049.

(−)-6Aj This product was obtained as a white solid in 87% yield and 85% ee from a reaction catalyzed by Q-4 (10 mol %) at 0° C. for 20 h.

General Procedure for Enantionselective Mannich Reaction of Malonate 5 to N-Cbz Amido Sulfones 1B

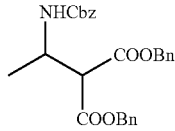

To a solution of N-Cbz α-amido sulfones 1B (0.40 mmol, 1.0 equiv), dibenzyl malonate 5 (0.60 mmol, 1.5 equiv) and QD-4 (0.040 mmol, 0.10 equiv) in methylene chloride (0.80 mL) at 0° C., was added chilled cesium hydroxide aqueous solution (0.10 M, 4.0 mL, 1.0 equiv) or cesium carbonate aqueous solution (0.10 M, 4.8 mL, 1.2 equiv) in one portion. The resulting biphasic reaction mixture was kept stirring at 0° C. for 20-96 h. Then the reaction mixture was diluted with water (10 mL) and extracted with ethyl ether (25 mL, three times). Organic layers were combined, washed with brine (30 mL), dried over anhydrous sodium sulfate and concentrated under reduced pressure. Crude product was purified by silica gel flash chromatography using the eluent specified below.

6Ba (+)-6Ba This product was obtained as a colorless oil (121 mg) in 64% yield after flash chromatography (silica gel: Hexanes/Methylene chloride=1/10 to remove malonate then eluent was changed to Hexanes/Ethyl Acetate=10/1) and in 91% ee as determined by HPLC [Daicel Chiralcel AD, Hexanes/IPA=80/20, 1.0 ml·min$^{-1}$, λ=220 nm, 20.0° C., $t_r$ (major)=15.92 min, $t_r$ (minor)=12.31 min] from a reaction catalyzed by QD-4 (10 mmol %) in methylene chloride (0.80 mL) and cesium hydroxide aqueous solution (0.10 M, 4.0 mL) at 0° C. for 20 h. [α]$_D^{25}$=17.9 (c=1.02, CHCl$_3$); $^1$H NMR (400 MHz, CDCl$_3$) δ 1.25 (d, J=6.8 Hz, 3H), 3.69 (d, J=3.6 Hz, 1H), 4.46 (brs, 1H), 5.00-5.20 (m, 6H), 5.62 (d, J=8.8 Hz, 1H), 7.22-7.36 (m, 15H); $^{13}$C NMR (100 MHz, CDCl$_3$) δ 19.29, 46.82, 56.09, 66.90, 67.57, 67.67, 128.23, 128.29, 128.50, 128.54, 128.63, 128.71, 128.79, 128.82, 135.23, 135.27, 136.67, 155.71, 167.54, 168.06; IR (neat) v 3434, 17319, 1560, 1508, 1216, 1152; HRMS: calc'd for (M+H)$^+$ C$_{27}$H$_{28}$NO$_6$Na: 462.1917; found 462.1929.

(−)-6Ba This product was obtained as a colorless oil (132 mg) in 70% yield and in 93% ee from a reaction catalyzed by Q-4 (10 mmol %) in methylene chloride (0.80 mL) and cesium carbonate aqueous solution (0.10 M, 4.8 mL) at 0° C. for 72 h.

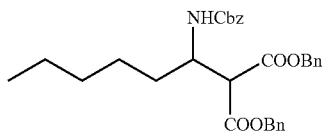

6Bb (+)-6Bb This product was obtained as a colorless oil (163 mg) in 78% yield after flash chromatography (silica gel: Hexanes/Methylene chloride=1/10 to remove malonate, then eluent was changed to Hexanes/Ethyl Acetate=10/1) and in 93% ee as determined by HPLC [Daicel Chiralcel OD, Hexanes/IPA=90/10, 1.0 ml·min$^{-1}$, λ=220 nm, 20.0° C., t$_r$ (major)=13.97 min, t$_r$ (minor)=12.80 min] from a reaction catalyzed by QD-4 (10 mmol %) in methylene chloride (0.80 mL) and cesium hydroxide aqueous solution (0.10 M, 4.0 mL) at 0° C. for 20 h. [α]$_D^{25}$=28.4 (c=1.01, CHCl$_3$); $^1$H NMR (400 MHz, CDCl$_3$) δ 0.84 (t, J=6.8 Hz, 3H), 1.15-1.38 (m, 6H), 1.40-1.60 (m, 2H), 3.71 (d, J=4.4 Hz, 1H), 4.26-4.38 (m, 1H), 4.98-5.16 (m, 4H), 5.15 (s, 2H), 5.62 (d, J=9.6 Hz, 1H), 7.24-7.36 (m, 15H); $^{13}$C NMR (100 MHz, CDCl$_3$) δ 13.88, 22.34, 35.78, 31.25, 33.41, 50.88, 54.89, 66.53, 67.19, 67.38, 127.87, 127.91, 128.25, 128.27, 128.35, 128.39, 128.45, 128.50, 134.96, 135.00, 136.51, 155.79, 167.39, 167.95; IR (neat) v 3420, 2930, 1734, 1722, 1507, 1499, 1218; HRMS: calc'd for (M+H)$^+$ C$_{31}$H$_{36}$NO$_6$: 518.2543; found 518.2556.

(−)-6Bb This product was obtained as a colorless oil (155 mg) in 75% yield and in 91% ee from a reaction catalyzed by Q-4 (10 mmol %) in methylene chloride (0.40 mL) and cesium hydroxide aqueous solution (0.10 M, 4.0 mL) at 0° C. for 20 h.

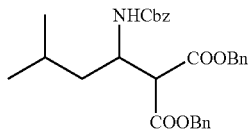

6Bc (+)-6Bc This product was obtained as a colorless oil (178 mg) in 88% yield after flash chromatography (silica gel: Hexanes/Methylene chloride=1/10 to remove malonate, then eluent was changed to Hexanes/Ethyl Acetate=10/1) and in 91% ee as determined by HPLC [Daicel Chiralcel AD, Hexanes/IPA=90/10, 1.0 ml·min$^{-1}$, λ=220 nm, 20.0° C., t$_r$ (major)=18.81 min, t$_r$ (minor)=16.44 min] from a reaction cata-lyzed by QD-4 (10 mmol %) in methylene chloride (0.80 mL) and cesium hydroxide aqueous solution (0.10 M, 4.0 mL) at 0° C. for 20 h. [α]$_D^{25}$=33.2 (c=1.00, CHCl$_3$); $^1$H NMR (400 MHz, CDCl$_3$) δ 0.86 (d, J=6.0 Hz, 3H), 0.87 (d, J=6.0 Hz, 3H), 1.18-1.28 (m, 1H), 1.48-1.64 (m, 2H), 3.69 (d, J=4.4 Hz, 1H), 4.43 (m, 1H), 5.00-5.12 (m, 4H), 5.15 (s, 2H), 5.56 (d, J=9.6 Hz, 1H), 7.20-7.40 (m, 15H); $^{13}$C NMR (100 MHz, CDCl$_3$) δ 21.71, 22.88, 24.82, 42.22, 49.02, 55.21, 66.55, 67.12, 67.35, 127.88, 127.92, 128.28, 128.35, 128.39, 128.45, 128.50, 134.97, 135.04, 136.48, 155.71, 167.38, 167.91; IR (neat) v 2957, 1735, 1560, 1508, 1217; HRMS: calc'd for (M+H)$^+$ C$_{30}$H$_{34}$NO$_6$: 504.2386; found 504.2383.

(−)-6Bc This product was obtained as a colorless oil (163 mg) in 81% yield and in 91% ee from a reaction catalyzed by Q-4 (10 mmol %) in methylene chloride (0.40 mL) and cesium carbonate aqueous solution (0.10 M, 4.8 mL) at 0° C. for 72 h.

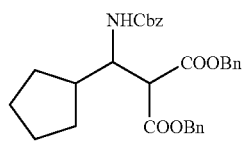

6Bd (+)-6Bd This product was obtained as a colorless oil (144 mg) in 70% yield after flash chromatography (silica gel: Hexanes/Methylene chloride=1/10 to remove malonate, then eluent was changed to Hexanes/Ethyl Acetate=10/1) and in 85% ee as determined by HPLC [Daicel Chiralcel AD, Hexanes IPA=80/20, 1.0 ml·min$^{-1}$, λ=220 nm, 20.0° C., t$_r$ (major)=12.50 min, t$_r$ (minor)=10.31 min] from a reaction catalyzed by QD-4 (10 mmol %) in methylene chloride (0.80 mL) and cesium hydroxide aqueous solution (0.10 M, 4.0 mL) at 0° C. for 20 h. [α]$_D^{25}$=33.3 (c=1.02, CHCl$_3$); $^1$H NMR (400 MHz, CDCl$_3$) δ 1.10-1.20 (m, 1H), 1.30-1.74 (m, 7H), 1.84-1.98 (m 1H), 3.73 (d, J=4.0 Hz, 1H), 4.21 (dt, J=3.6, 10.4 Hz, 1H), 4.94-5.22 (m, 6H), 5.90 (d, J=10.4 Hz, 1H), 7.20-7.40 (m, 15H); $^{13}$C NMR (100 MHz, CDCl$_3$) δ 24.79, 25.26, 29.82, 30.18, 44.15, 54.28, 55.50, 66.47, 67.19, 67.47, 127.79, 127.84, 128.21, 128.25, 128.32, 128.35, 128.42, 128.50, 134.96, 135.01, 136.64, 155.93, 167.42, 168.35; IR (neat) v 3428, 2954, 1730, 1501, 1218; HRMS: calc'd for (M+H)$^+$ C$_{31}$H$_{34}$NO$_6$: 516.2386; found 516.2402.

(−)-6Bd This product was obtained as a colorless oil (134 mg) in 67% yield and in 82% ee from a reaction catalyzed by Q-4 (10 mmol %) in methylene chloride (0.80 mL) and cesium carbonate aqueous solution (0.10 M, 4.8 mL) at 0° C. for 96 h.

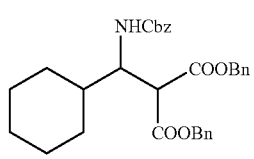

6Be (+)-6Be This product was obtained as a white solid (156 mg) in 73% yield after flash chromatography (silica gel: Hexanes/Methylene chloride=1/10 to remove malonate, then eluent was changed to Hexanes/Ethyl Acetate=10/1) and in 90% ee as determined by HPLC [Regis Pirckle Covalent (R, R) Whelk-O 1, Hexanes/IPA=92/8, 1.0 ml·min$^{-1}$, λ=220 nm, 20.0° C., $t_r$ (major)=10.74 min, $t_r$ (minor)= 12.80 min] from a reaction catalyzed by QD-4 (10 mmol %) in methylene chloride (0.40 mL) and cesium carbonate aqueous solution (0.10 M, 4.8 mL) at 0° C. for 96 h. $[\alpha]_D^{25}$=35.6 (c=1.04, CHCl$_3$); $^1$H NMR (400 MHz, CDCl$_3$) δ 0.84-1.14 (m, 5H), 1.26-1.40 (m, 1H), 1.48-1.86 (m, 5H), 3.81 (d, J=4.4 Hz, 1H), 4.12 (dt, J=3.6, 10.0 Hz, 1H), 5.01 (dd, J=12.4, 40.0 Hz, 2H), 5.03 (s, 2H), 5.17 (dd, J=12.0, 28.0 Hz, 2H), 5.81 (d, J=10.4 Hz, 1H), 7.28-7.40 (m, 15H); $^{13}$C NMR (100 MHz, CDCl$_3$) δ 25.65, 25.72, 25.94, 41.03, 52.58, 55.72, 66.50, 67.19, 67.50, 127.86, 128.28, 128.32, 128.42, 128.51, 135.00, 136.64, 156.07, 167.83, 168.37; IR (neat) ν 3424, 2929, 1730, 1501, 1214; HRMS: calc'd for (M+H)$^+$ C$_{32}$H$_{36}$NO$_6$: 530.2543; found 530.2546.

(−)-6Be This product was obtained as a colorless oil (134 mg) in 81% yield and in 87% ee from a reaction catalyzed by Q-4 (10 mmol %) in methylene chloride (0.40 mL) and cesium carbonate aqueous solution (0.10 M, 4.8 mL) at 0° C. for 96 h.

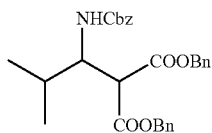

6Bf (+)-6Bf This product was obtained as a colorless oil (132 mg) in 67% yield after flash chromatography (silica gel: Hexanes/Methylene chloride=1/10 to remove malonate, then eluent was changed to Hexanes/Ethyl Acetate=10/1) and in 85% ee as determined by HPLC [Daicel Chiralpak AD, Hexanes/IPA=90/10, 1.0 ml·min$^{-1}$, λ=220 nm, 20.0° C., $t_r$ (major)=19.92 min, $t_r$ (minor)=14.56 min] from a reaction catalyzed by QD-4 (10 mmol %) in methylene chloride (0.40 mL) and cesium carbonate aqueous solution (0.10 M, 4.8 mL) at 0° C. for 96 h. $[\alpha]_D^{25}$=31.2 (c=1.01, CHCl$_3$); $^1$H NMR (400 MHz, CDCl$_3$) δ 0.89 (d, J=6.8 Hz, 3H), 0.94 (d, J=7.2 Hz, 3H), 1.68-1.80 (m, 1H), 3.80 (d, J=3.6 Hz, 1H), 4.11 (dt, J=3.6, 10.0 Hz, 1H), 4.95-5.01 (m, 4H), 5.16 (s, 2H), 5.82 (d, J=10.4 Hz, 1H), 7.28-7.40 (m, 15H); $^{13}$C NMR (100 MHz, CDCl$_3$) δ 19.24, 19.77, 31.93, 53.10, 56.65, 66.55, 67.30, 67.56, 127.88, 127.91, 128.26, 128.33, 128.38, 128.44, 128.47, 128.55, 134.93, 134.99, 136.66, 156.08, 167.70, 168.35; IR (neat) ν 3420, 2929, 1729, 1218; HRMS: calc'd for (M+H)$^+$ C$_{29}$H$_{32}$NO$_6$: 490.2230; found 490.2248.

(−)-6Bf This product was obtained as a colorless oil (138 mg) in 70% yield and in 82% ee from a reaction catalyzed by Q-4 (10 mmol %) in methylene chloride (0.40 mL) and cesium carbonate aqueous solution (0.10 M, 4.8 mL) at 0° C. for 96 h.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of forming a chiral non-racemic amine, comprising the step of: combining in a halohydrocarbon solvent a nucleophile selected from the group consisting of malonates and keto esters, a base selected from the group consisting of carbonates and hydroxides, a chiral non-racemic catalyst, and a substrate selected from the group consisting of N-alkoxycarbonyl imine, N-aryloxycarbonyl imine, N-alkenyloxycarbonyl imine, N-aralkoxycarbonyl imine, and N-aralkenyloxycarbonyl imine; wherein said chiral non-racemic catalyst is (DHQ)$_2$PHAL, (DHQD)$_2$PHAL, (DHQ)$_2$PYR, (DHQD)$_2$PYR, (DHQ)$_2$AQN, (DHQD)$_2$AQN, DHQ-CLB, DHQD-CLB, DHQ-MEQ, DHQD-MEQ, DHQ-AQN, DHQD-AQN, DHQ-PHN, DHQD-PHN, QD-PH, QD-AN, QD-NT, QD-AC, QD-CH, QD-IP, QD-(−)-MN, QD-AD, Q-PH, Q-AN, Q-NT, Q-CH, Q-AC, Q-IP, Q-(−)-MN, Q-AD, 9-thiourea Q or 9-thiourea QD; said chiral non-racemic catalyst catalyzes the addition of said nucleophile to said substrate to give a chiral non-racemic amine; the enantiomeric excess or diastereomeric excess of the chiral non-racemic amine is greater than about 90%; and the method is performed at a temperature in the range of −20° C. to 50° C.

2. The method of claim 1, wherein said substrate is an N-alkoxycarbonyl imine, N-alkenyloxycarbonyl imine or N-aralkoxycarbonyl imine.

3. The method of claim 1, wherein said substrate is an N-allyloxycarbonyl imine, N-benzyloxycarbonyl imine, N-tert-butoxycarbonyl imine, N-2,2,2-trichloroethoxycarbonyl imine, 2-(trimethylsilyl)ethoxycarbonyl imine or N-9-fluorenylmethoxycarbonyl imine.

4. The method of claim 1, further comprising: combining an N-α-phosphonylalkyl O-alkyl carbamate, N-α-sulfonylalkyl O-alkyl carbamate, N-α-haloalkyl O-alkyl carbamate, N-α-phosphonylalkyl O-aryl carbamate, N-α-sulfonylalkyl O-aryl carbamate, N-α-haloalkyl O-aryl carbamate, N-α-phosphonylalkyl O-alkenyl carbamate, N-α-sulfonylalkyl O-alkenyl carbamate, N-α-haloalkyl O-alkenyl carbamate, N-α-phosphonylalkyl O-aralkyl carbamate, N-α-sulfonylalkyl O-aralkyl carbamate, N-α-haloalkyl O-aralkyl carbamate, N-α-phosphonylalkyl O-aralkenyl carbamate, N-α-sulfonylalkyl O-aralkenyl carbamate, or N-α-haloalkyl O-aralkenyl carbamate, and a base to generate an N-alkoxycarbonyl imine, N-aryloxycarbonyl imine, N-alkenyloxycarbonyl imine, N-aralkoxycarbonyl imine, or N-aralkenyloxycarbonyl imine.

5. The method of claim 1, further comprising: combining an N-α-sulfonylalkyl O-alkyl carbamate, N-α-sulfonylalkyl O-aryl carbamate, N-α-sulfonylalkyl O-alkenyl carbamate, N-α-sulfonylalkyl O-aralkyl carbamate, or N-α-sulfonylalky O-aralkenyl carbamate, and a base to generate an N-alkoxycarbonyl imine, N-aryloxycarbonyl imine, N-alkenyloxycarbonyl imine, N-aralkoxycarbonyl imine, or N-aralkenyloxycarbonyl imine.

6. The method of claim 1, wherein said nucleophile is a malonate.

7. The method of claim 1, wherein said chiral non-racemic catalyst is 9-thiourea Q or 9-thiourea QD.

8. The method of claim 1, wherein said chiral non-racemic catalyst is represented by QD or Q:

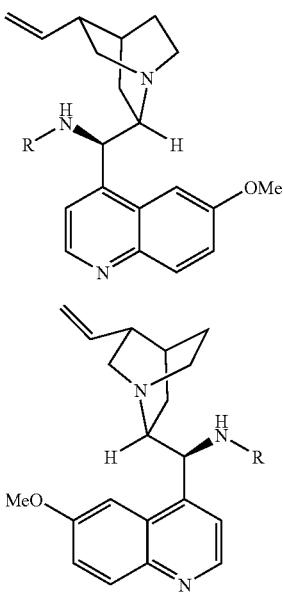

QD

Q wherein
R represents hydrogen, alkyl, aryl, acyl, alkynyl, heteroaryl, cycloalkyl, cycloalkenyl, aralkyl, heteroaralkyl, heteroalkyl, alkoxycarbonyl, aryloxycarbonyl, alkenyloxycarbonyl, aralkoxycarbonyl, aralkenyloxycarbonyl, alkylaminocarbonyl, arylaminocarbonyl, aralkylaminocarbonyl, aminocarbonyl, alkenylaminocarbonyl, aralkenylaminocarbonyl, alkylthiocarbonyl, arylthiocarbonyl, aryloxythiocarbonyl, alkoxythiocarbonyl, aralkoxythiocarbonyl, arylaminothiocarbonyl, aralkylaminothiocarbonyl, alkenyloxythiocarbonyl, alkenylaminothiocarbonyl, aminothiocarbonyl, alkylaminothiocarbonyl, aralkenyloxythiocarbonyl, aralkenylaminothiocarbonyl, alkylsulfonyl, arylsulfonyl, aralkylsulfonyl, alkenylsulforyl, arylphosphoryl, aralkylphosphoryl, alkenylphosphoryl or alkylphosphoryl.

9. The method of claim 8, wherein R is arylaminothiocarbonyl.

10. The method of claim 8, wherein R is 3,5-bis(trifluoromethyl)phenylaminothiocarbonyl.

11. The method of claim 1, wherein said base is a hydroxide.

12. The method of claim 1, wherein said substrate is an N-alkoxycarbonyl imine, N-alkenyloxycarbonyl imine or N-aralkoxycarbonyl imine; and said nucleophile is a malonate.

13. The method of claim 1, wherein said substrate is an N-alkoxycarbonyl imine, N-alkenyloxycarbonyl imine or N-aralkoxycarbonyl imine; and said nucleophile is a malonate; and said base is a hydroxide.

14. The method of claim 1, wherein said substrate is an N-alkoxycarbonyl imine, N-alkenyloxycarbonyl imine or N-aralkoxycarbonyl imine; and said nucleophile is a malonate; and said base is a hydroxide; and said chiral non-racemic catalyst is (DHQ)₂PHAL, (DHQD)₂PHAL, (DHQ)₂PYR, (DHQD)₂PYR, (DHQ)₂AQN, (DHQD)₂AQN, DHQ-CLB, DHQD-CLB, DHQ-MEQ, DHQD-MEQ, DHQ-AQN, DHQD-AQN, DHQ-PHN, DHQD-PHN, QD-PH, QD-AN, QD-NT, QD-AC, QD-CH, QD-IP, QD-(−)-MN, QD-AD, Q-PH, Q-AN, Q-NT, Q-CH, Q-AC, Q-IP, Q-(−)-MN, Q-AD, 9-thiourea Q or 9-thiourea QD.

15. The method of claim I, wherein said substrate is an N-alkoxycarbonyl imine, N-alkenyloxycarbonyl imine or N-aralkoxycarbonyl imine; and said nucleophile is a malonate; and said base is a hydroxide; and said chiral non-racemic catalyst is 9-thiourea Q or 9-thiourea QD.

16. A method of preparing a chiral non-racemic amine represented by Scheme 1:

Scheme 1

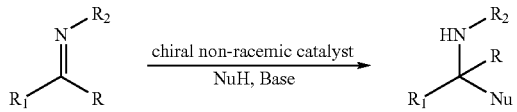

wherein
said chiral non-racemic catalyst is represented by QD or Q:

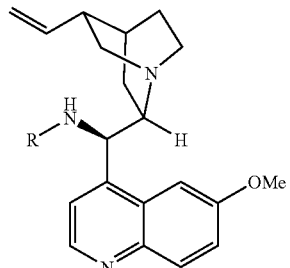

QD

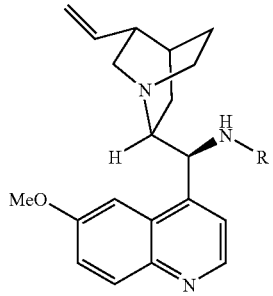

Q wherein
R represents hydrogen, alkyl, aryl, acyl, alkynyl, heteroaryl, cycloalkyl, cycloalkenyl, aralkyl, heteroaralkyl, heteroalkyl, alkoxycarbonyl, aryloxycarbonyl, alkenyloxycarbonyl, aralkoxycarbonyl, aralkenyloxycarbonyl, alkylaminocarbonyl, arylaminocarbonyl, aralkylaminocarbonyl, aminocarbonyl, alkenylaminocarbonyl, aralkenylaminocarbonyl, alkylthiocarbonyl, arylthiocarbonyl, aryloxythiocarbonyl, alkoxythiocarbonyl, aralkoxythiocarbonyl, arylaminothiocarbonyl, aralkylaminothiocarbonyl, alkenyloxythiocarbonyl, alkenylaminothiocarbonyl, aminothiocarbonyl, alkylaminothiocarbonyl, aralkenyloxythiocarbonyl, aralkenylaminothiocarbonyl, alkylsulfonyl, arylsulfonyl, aralkylsulfonyl, alkenylsulforyl, arylphosphoryl, aralkylphosphoryl, alkenylphosphoryl or alkylphosphoryl;

R' represents hydrogen, alkyl, aryl, heteroaryl, cycloalkyl, aralkyl, or heteroaralkyl;

$R_1$ represents alkyl, aryl, heteroaryl, cycloalkyl, aralkyl, or heteroaralkyl;

R' and $R_1$, taken together, may form an optionally substituted ring consisting of 3-10 backbone atoms inclusive; said ring optionally comprising one or more hetereoatoms;

$R_1$ and $R_2$, taken together, may form an optionally substituted ring consisting of 4-10 backbone atoms inclusive; said ring optionally comprising one or more hetereoatoms beyond the nitrogen to which $R_2$ is bonded;

$R_2$ represents alkoxycarbonyl, aryloxycarbonyl, alkenyloxycarbonyl, aralkoxycarbonyl, or aralkenyloxycarbonyl;

NuH represents malonate or keto ester;

base represents carbonate or hydroxide;

the method is performed in a halohydrocarbon solvent; and the method is performed at a temperature in the range of −20° C. to 50° C.;

wherein the enantiomeric excess or diastereomeric excess of the chiral non-racemic amine is greater than about 90%.

17. The method of claim 16, wherein $R_2$ represents alkoxycarbonyl, alkenyloxycarbonyl or aralkoxycarbonyl.

18. The method of claim 16, wherein NuH represents malonate.

19. The method of claim 16, wherein base represents hydroxide.

20. The method claim 16, wherein $R_2$ represents alkoxycarbonyl, alkenyloxycarbonyl or aralkoxycarbonyl; and NuH represents malonate.

21. The method claim 16, wherein $R_2$ represents alkoxycarbonyl, alkenyloxycarbonyl or aralkoxycarbonyl; and NuH represents malonate; and base represents hydroxide.

22. The method of claim 16, wherein R is arylaminothiocarbonyl.

23. The method of claim 16, wherein R is 3,5-bis(trifluoromethyl)phenylaminothiocarbonyl.

24. The method of claim 1, wherein the method is performed at a temperature in the range of −20° C. to 25° C.

25. The method of claim 16, wherein the method is performed at a temperature in the range of −20° C. to 25° C.

26. The method of claim 1, wherein the method is performed at room temperature.

27. The method of claim 1, wherein the halohydrocarbon solvent is methylene chloride or chloroform.

28. The method of claim 16, wherein the method is performed at room temperature.

29. The method of claim 16, wherein the halohydrocarbon solvent is methylene chloride or chloroform.

* * * * *